(12) United States Patent
Omernick et al.

(10) Patent No.: US 8,325,875 B2
(45) Date of Patent: Dec. 4, 2012

(54) PORTABLE RADIOLOGICAL IMAGING SYSTEM

(75) Inventors: Jon Charles Omernick, Wauwatosa, WI (US); Rajeev Ramankutty Marar, Waukesha, WI (US); Jonathan Mark Butzine, Oconomowoc, WI (US)

(73) Assignee: General Electric Company, Schenectady, NY (US)

( * ) Notice: Subject to any disclaimer, the term of this patent is extended or adjusted under 35 U.S.C. 154(b) by 235 days.

(21) Appl. No.: 12/786,371

(22) Filed: May 24, 2010

(65) Prior Publication Data

US 2011/0286575 A1 Nov. 24, 2011

(51) Int. Cl.
*H05G 1/64* (2006.01)
*G01N 23/04* (2006.01)

(52) U.S. Cl. .......................................... 378/62; 378/98.8
(58) Field of Classification Search ................. 378/98.8, 378/62, 63, 102, 108; 250/580, 370.09
See application file for complete search history.

(56) References Cited

U.S. PATENT DOCUMENTS

| | | | |
|---|---|---|---|
| 7,261,465 B2* | 8/2007 | Butzine et al. ................ | 378/198 |
| 7,298,825 B2 | 11/2007 | Omernick et al. | |
| 2006/0261296 A1* | 11/2006 | Heath et al. ................... | 250/580 |
| 2007/0189462 A1* | 8/2007 | Spahn .......................... | 378/193 |
| 2009/0118606 A1 | 5/2009 | Jabri et al. | |
| 2009/0129546 A1 | 5/2009 | Newman et al. | |

* cited by examiner

*Primary Examiner* — Irakli Kiknadze
(74) *Attorney, Agent, or Firm* — Fletcher Yoder, P.C.

(57) ABSTRACT

In one embodiment, a portable radiological imaging system includes a portable base station having an X-ray source and a power supply, a wireless X-ray detector configured to receive X-ray radiation from the source and to generate image data based upon the received radiation, and a portable image processing system removably carried by the base station and configured to receive the image data from the detector and to process the image data to produce and display a user-viewable image derived from the image data.

23 Claims, 4 Drawing Sheets

PORTABLE RADIOLOGICAL IMAGING SYSTEM

BACKGROUND OF THE INVENTION

The subject matter disclosed herein relates to X-ray imaging systems and more particularly to mobile radiography.

In the hospital setting, mobile radiographic exams are performed on patients difficult to move or incapable of being moved. Also, in tertiary care medical centers, mobile radiographic exams represent a significant percentage of radiographic exams performed.

Many of the earlier mobile radiographic imaging systems employ conventional X-ray imaging using film and/or computed radiography. In order to obtain images from these systems, the imaging medium must be transported and processed after each exposure, resulting in a time delay in obtaining the desired images. Digital radiography provides an alternative that allows the acquisition of image data and reconstructed images on the spot for quicker viewing and diagnosis. However, the cost of replacing the earlier mobile radiographic imagining systems with digital radiographic imaging systems may be imposing to a hospital or tertiary care medical center. Hence, the need to retrofit the earlier mobile radiographic imaging systems for digital radiography.

BRIEF DESCRIPTION OF THE INVENTION

In accordance with one embodiment, a portable radiological imaging system includes a portable base station having an X-ray source and a power supply, a wireless X-ray detector configured to receive X-ray radiation from the source and to generate image data based upon the received radiation, and a portable image processing system removably carried by the base station and configured to receive the image data from the detector and to process the image data to produce and display a user-viewable image derived from the image data.

In accordance with another embodiment, a portable radiological imaging system includes a portable image processing system separate from and configured to be removably carried by an X-ray source base station, the processing system comprising a wireless receiver for receiving the image data wirelessly from an X-ray detector, a computer configured to execute an image reconstruction routine to derive the user-viewable image from the image data, and a user-viewable screen coupled to the computer for displaying the user-viewable image.

In accordance with a further embodiment, a method for operating a portable radiological imaging system includes removably mounting a portable processing system on a portable base station. The base station includes an X-ray source, a power supply, and a holder for the portable processing system. The portable processing system includes a wireless receiver for receiving the image data wirelessly from an X-ray detector, a computer configured to execute an image reconstruction routine to derive the user-viewable image from the image data, and a user viewable screen coupled to the computer for displaying the user-viewable image.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION OF THE INVENTION

Figure 1:
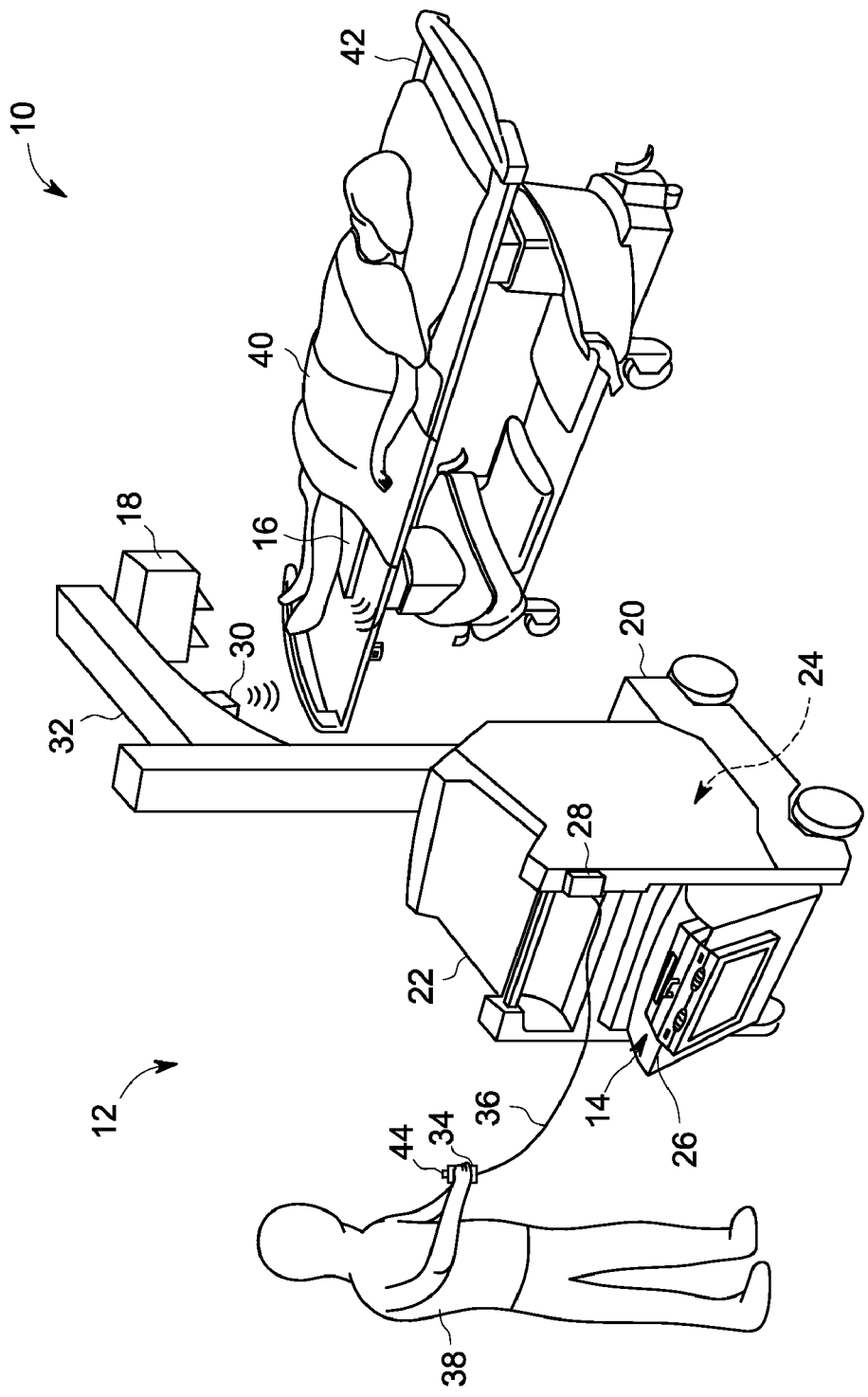
FIG. 1 is a perspective view of a portable radiological imaging system, in accordance with aspects of the present technique.

Referring generally to FIG. 1, a portable radiological imaging system is represented, referenced generally by reference numeral 10. In the illustrated embodiment, the imaging system 10, as adapted, is a digital X-ray system designed both to acquire original image data and to process the image data for display of X-ray images.

In the embodiment illustrated in FIG. 1, the portable radiological imaging system 10 includes a portable base station 12, a portable image processing system 14, and a wireless X-ray detector 16. The portable base station 12 has an X-ray source 18 and a wheeled base 20 attached to a base unit 22 for moving the portable base station 12. The base unit 22 houses systems electronic circuitry 24 that both provides and controls power to the X-ray source 18. The power for the X-ray source 18 is provided by a power supply, such as one or more batteries. The power provided by the power supply also supplies power to operate the wheeled base 20 (i.e., to drive one or more motors in the base).

The X-ray detector 16 is configured to receive X-ray radiation from the X-ray source 18 and to generate image data based upon the received radiation. The portable image processing system 14 is configured to receive the image data from the detector 16 through wireless receiver 56 and to process the image data to produce and display a user-viewable image derived from the image data. The portable image processing system 14 is located and carried in a bin or holder 26 within the portable base station 12. Most of the portable image processing system 14 fits into the holder 26 and the holder 26 may be closed, thereby enclosing most of the system 14. The portable image processing system 14 is removable and can be used with other portable base stations 12. That is, when the system 14 is to be used with the base station 12, a bin door or other cover can be opened, the system 14 placed inside, with part of it extending (e.g., for image viewing, as described below), and the detector 16 removed when needed for data generation during an X-ray exposure.

The portable base station 12 also has a real-time handswitch interface 28 attached to the base unit 22, and a wireless antenna 30. The wireless antenna 30 may be located on the base unit 22, under an arm 32 of the portable base station 12, near the X-ray source 18, or may be integrated into the handswitch interface 28. The wireless antenna 30 allows the portable base station 12 to communicate wirelessly with the portable image processing system 14. The real-time handswitch interface 28 is connected to the system electronic circuitry 24 to control the acquisition of images using the X-ray source 18. The real-time handswitch interface 28 wirelessly communicates with the image processing system 14 via the wireless antenna 30 or through an independent wireless connection (Zigbee for example) between the handswitch interface 28 and the processing unit 14. Alternatively, the real-time handswitch interface 28 may be connected to the portable image processing system 14 by a wired connection.

A handswitch 34 is connected to the real-time handswitch interface 28 via a cord 36. Input by a user 38 via the handswitch 34 prepares the X-ray source 18, resets the detector 16, and commands an X-ray exposure following the minimum preparation time.

More specifically, a patient 40 is located between the X-ray source 18 and the detector 16 on an examination table or bed 42. The user 38 initiates the acquisition of an image by pressing a preparation switch located on the handswitch 34, thereby generating a preparation signal. The X-ray source 18 is prepared in response to the preparation signal by initiating spinning of a rotor housing the X-ray source 18. In addition, the detector 16 receives the preparation signal via the wireless receiver 56 from handswitch interface 28 through antenna 30 and increases the detector power mode from low to high. Then, the user 38 presses an exposure switch located on the handswitch 34 to generate an exposure signal. The preparation and exposure switches may have separate buttons on the handswitch 34. Alternatively, the preparation and exposure switches may be embodied in a single button 44 that can be depressed in two positions, a first position for the preparation signal and second position for the exposure signal. Upon the user 38 pressing the exposure switch, the detector 16 receives via the wireless receiver 56 from handswitch interface 28 through antenna 30, a signal to stop scrub and prepare the detector circuitry for an exposure. Such scrubbing prior to exposure may involve recharging photodiodes of the detector 16 so as to prepare the detector 16 for receipt of radiation and resulting generation of image data. After detector ready received (scrub completed), the detector 16 receives X-rays that pass through the patient 40 and transmits imaging data to the portable image processing system 14. Handswitch interface 28 may delay sending exposure switch status until detector 16 has indicated it is ready for exposure or disable exposure if detector is not ready. The portable image processing system 14 receives and processes the imaging data to generate the image. Images generated by the portable radiological imaging system 10 may be sent wirelessly to a server, such as picture archiving communication system (PACS) and/or a radiology department information system (RIS) or hospital information system (HIS). In addition to use with the digital detector 16, the portable base station 12 may be operated in analog mode using film and/or a computed radiography cassette in a conventional manner.

Figure 2:
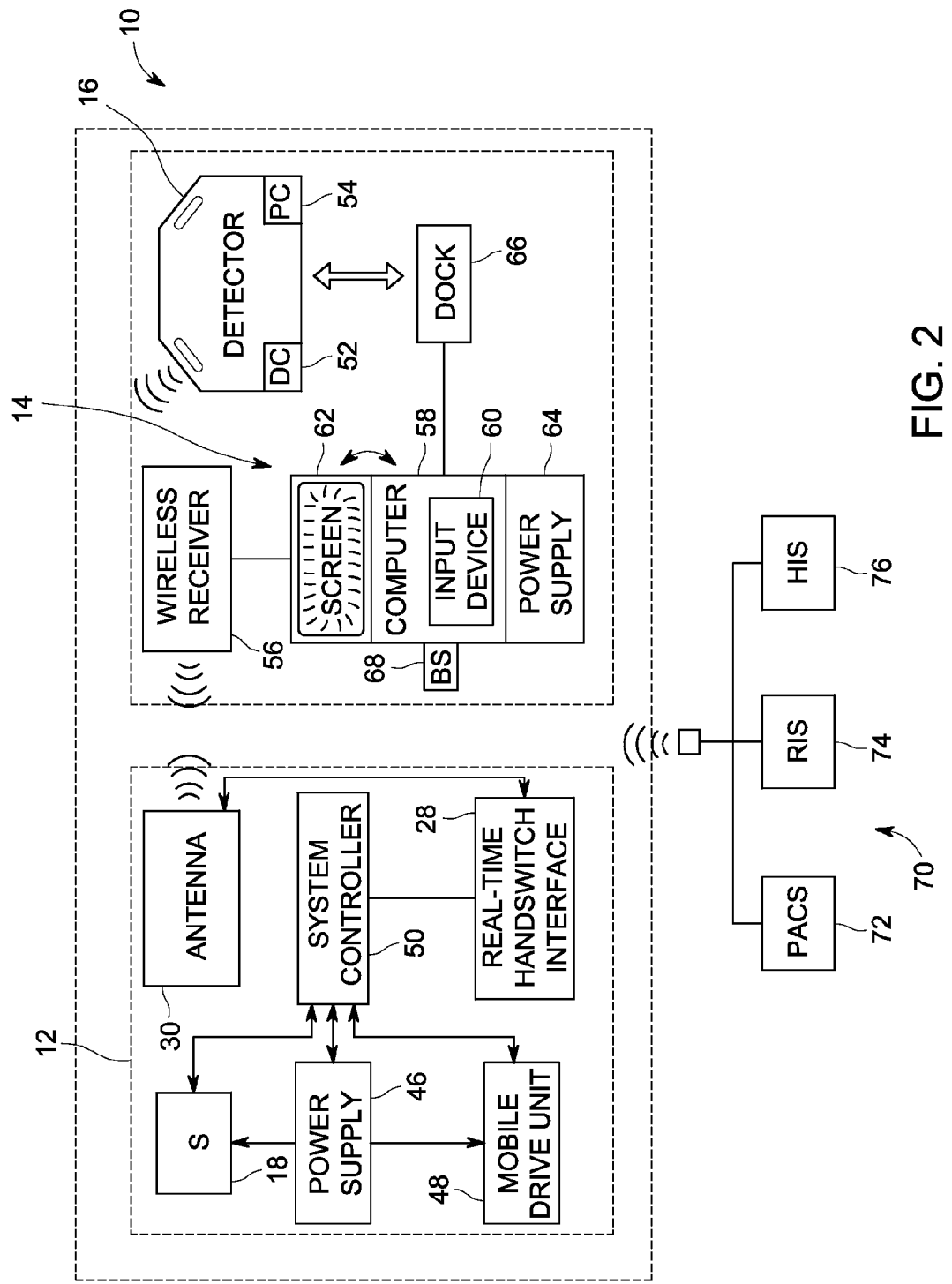
FIG. 2 is a diagrammatical overview of the portable radiological imaging system of FIG. 1.

FIG. 2 illustrates diagrammatically the portable radiological imaging system 10 of FIG. 1. The X-ray base station 12 includes the source of X-ray radiation 18. The source 18 is controlled by a power supply 46 which furnishes both power and control signals for examination sequences. In addition, the power supply 46 furnishes power to a mobile drive unit 48 of the wheeled base 24. Further, the power supply 46 is responsive to signals from a system controller 50, while also furnishing power to the system controller 50. In general, system controller 50 commands operation of the imaging system 10 to execute examination protocols, as well as operation of the mobile drive unit 48. In the present context, system controller 50 also includes signal processing circuitry, typically based upon a general purpose or application-specific digital computer, associated memory circuitry for storing programs and routines executed by the computer, as well as configuration parameters, interface circuits, and so forth. The system controller 50 is responsive to signals received from the handswitch interface 28, such as preparation and exposure signals generated by the user 38 using the handswitch 34. Further, the handswitch interface 28 may disable prepare and exposure signals from the handswitch 34 if either the detector 16 is not ready for an exposure or the portable image processing system 14 is installed, but not communicating with the handswitch interface 28 (backup sensing by handswitch interface 28 that image system 14 has been installed in holder 26 to avoid exposure without image). As mentioned above, the portable base station 12 has a wireless antenna 30, and the handswitch interface 28 communicates with the portable image processing system 14 via the antenna 30 or another independent wireless communication. The handswitch interface 28 may also communicate via a hardwire connection or other method (IR, etc.) between it and the portable image processing system 14. It is noted that the antenna may utilize any suitable wireless communication protocol, such as an ultra wideband (UWB) communication standard, a Bluetooth/Zigbee communication standard, or any 802.11 communication standard.

In the portable radiological imaging system 10, the detector 16 is coupled to a detector controller 52, which commands acquisition of the signals generated in the detector 16. The detector controller 52 may also execute various signal processing and filtration functions, such as for initial adjustment of dynamic ranges, interleaving of digital image data, and so forth. The detector controller 52 is responsive to signals from the image processing system 14. For example, an exposure signal sent from the handswitch interface 28 may be sent to the detector controller 52 to stop scrub of the detector 16 prior to exposure. A power supply 54 (e.g., a battery) furnishes power to the detector 16.

As mentioned above, the detector 16 communicates with the portable image processing system 14. The portable image processing system 14 includes a wireless receiver 56 to communicate with both the portable base station 12 and the detector 16. Wireless receiver 56 may also be split, independently communicating wirelessly. The portable image processing system 14 also includes a computer 58 configured to execute an image reconstruction routine to derive a user-viewable image from image data received by the wireless receiver 56 from the detector 16. Generally, the computer 58 includes signal processing circuitry, associated memory circuitry for storing programs and routines executed by the computer, as well as configuration parameters and image data, interface circuits, and so forth. The computer 58 includes an input device 60 to facilitate interaction between the user 38 and the portable radiological imaging system 10. The input device 60 may include a keyboard, mouse, and/or other device. The computer 58 is coupled to a user-viewable screen 62. The user-viewable screen 62 displays images the computer 50 derived from image data received from the detector 16. In addition, the screen 62 may display a hospital worklist (e.g., from the RIS or HIS) for image sequences to be performed by the portable radiological imaging system 10. The screen 62 is movable between a viewing position and a stowed position. In the stowed position, shown in FIGS. 1 and 3, the computer 58 is in low power mode and the screen 62 may not be illuminated to save power. In the viewing position, when the screen 62 is tilted up, the computer 58 is in full power mode and the screen 62 is illuminated for viewing. The portable image processing system 14 includes a power supply 64 configured to provide electrical power to the computer 58. The power supply 64 may include a battery module. The power supply 64 is rechargeable when placed in a charging station.

In addition, the portable image processing system 14 includes a dock 66 for holding the detector 16 when the detector 16 is not in use. The dock 66 protects the detector 16 from damage. In addition, the dock 66 allows the power supply 64 of the portable image processing system 14 to maintain a charge on the detector 16 when the detector 16 is located within the dock 66. When the detector 16 is first inserted in the dock 66, the dock 66 allows the detector 16 and the computer 58 to communicate. The detector 16 communicates to the computer 58 detector identification information, as well as, calibration parameters to be used.

Further, the portable image processing system 14 includes a bin sensor 68 connected to the computer 58. Upon insertion of the portable image processing system 14 into the holder 26 of the portable base station 12, the bin sensor 68 provides a signal to the computer 58 to wirelessly connect to the medical facility network system 70 which may include a variety of systems such as PACS 72, RIS 74, and/or HIS 76. The image processing system 14 receives data such as a hospital worklist for image sequences to be performed by the portable radiological imaging system 10.

Figure 3:
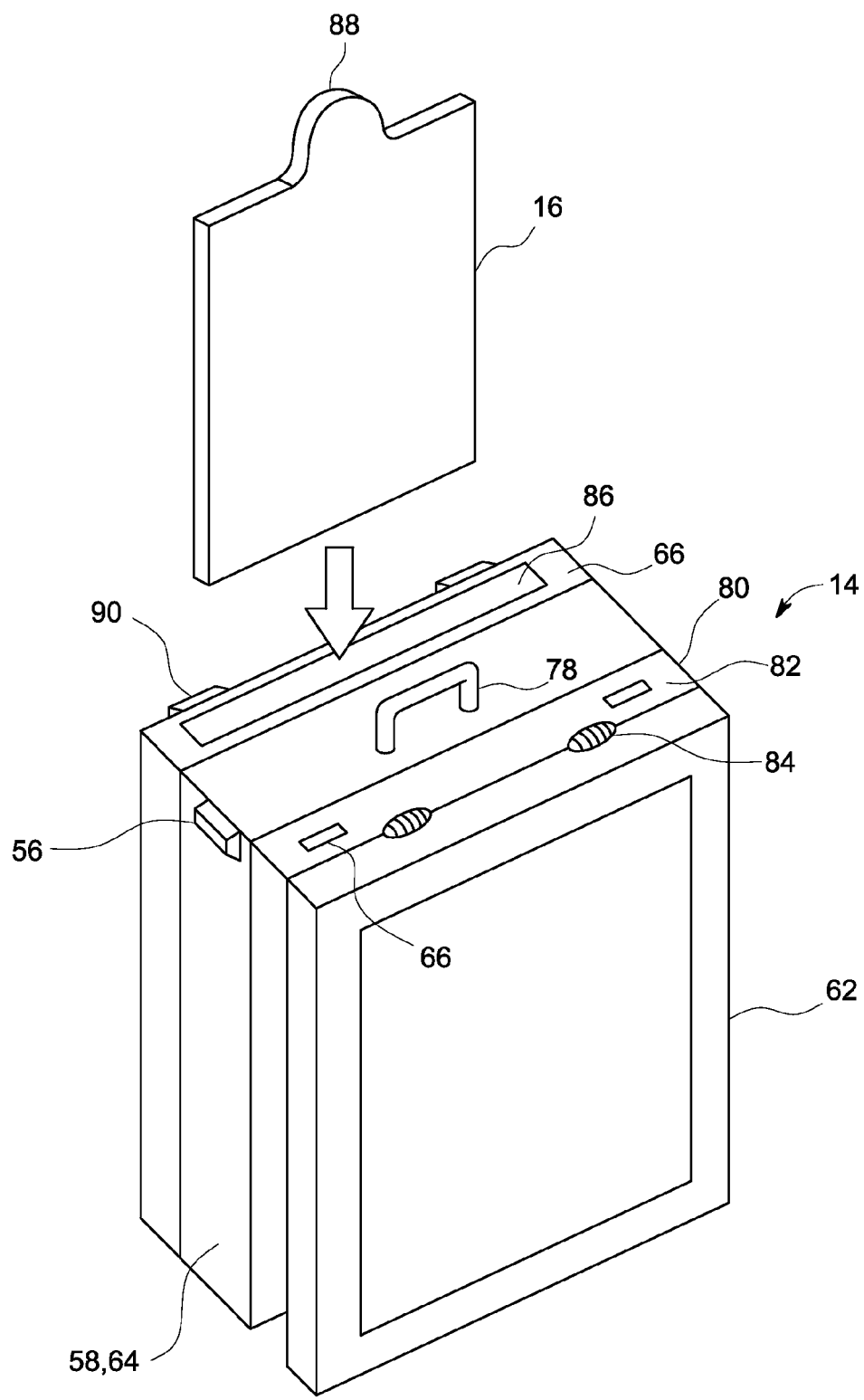
FIG. 3 is a perspective view of a portable image processing system of FIG. 1, in accordance with aspects of the present technique.

FIG. 3 illustrates the portable image processing system 14 in greater detail. In general, the portable image processing system 14 includes user-viewable screen 62, computer/power supply 58 and 64, and dock 66. The portable image processing system 14 has a handle 78 to transport the system 14, as well as to place into or to remove the system 14 from the holder 26 of the portable base station 12. Between the computer 58 and the screen 62, the portable image processing system 14 includes an overhang or extension 80. The overhang 80 extends over the top of the holder 26 allowing the screen 62 to extend from the holder 26, as illustrated in FIG. 1, while the rest of the portable image processing system 14 is stored in the holder 26. The overhang 80 has one or more bin sensors 68 located on a top surface 82 of the overhang to sense when the portable image processing system 14 is placed within the holder 26. Upon sensing the insertion of the portable image processing system 14, the computer 58 communicates wirelessly via the wireless receiver 56 with the medical facility's network system 70, as mentioned above, to acquire the worklist. The wireless receiver 56 is located on the computer 58. It should be noted that the particular physical arrangement of the system may be subject to a wide range of alternatives, and that shown and described in the present discussion is intended to be exemplary only. Handswitch interface 28 also senses insertion of image processing system 14 and prepares to communicate wirelessly to image processing system 14.

The screen 62 is connected to the computer 58 via one or more hinges 84 located between the interface of the overhang 80 and the screen 62. The hinges 84 allow the screen 62 to be folded down in a stowed position. Also, the hinges 84 allow the screen 62 to be extended or swiveled upward into a viewing position to view user-viewable images displayed on the screen 62. Further, hinges 84 provide input to switch from lower power mode to high power mode.

Located to the rear of the computer 58 is the dock 66 for holding the detector 16. The dock 66 has a slot 86 configured to receive the detector 16. Upon insertion of the detector 16, the dock 66 may at least partially enclose the detector 16, except the handle portion 88 of the detector 16, thus protecting the detector 16 from damage, while allowing it to be removed easily for imaging. As mentioned above, while the detector 16 is located within the dock 66, the power supply 64 of the portable image processing system 14 maintains a charge on the detector 16. The power supply 64 of image processing system 14 is sufficient to power the image processing system 14 over typical usage time, as well as the detector 16 when necessary. One or more magnets 90 or other latching mechanisms are attached to the backside of the dock 66. The magnets 90 allow the holder 26 to be placed in a nearly closed position when the portable image processing system 14 is located within the holder 26. In this presently contemplated arrangement, the portable base station 12 is not coupled to the image processing system 14, other than holding the system 14 in the holder 26. Alternatively, various physical (e.g., wired) connections could be made between the system and the base station.

Figure 4:
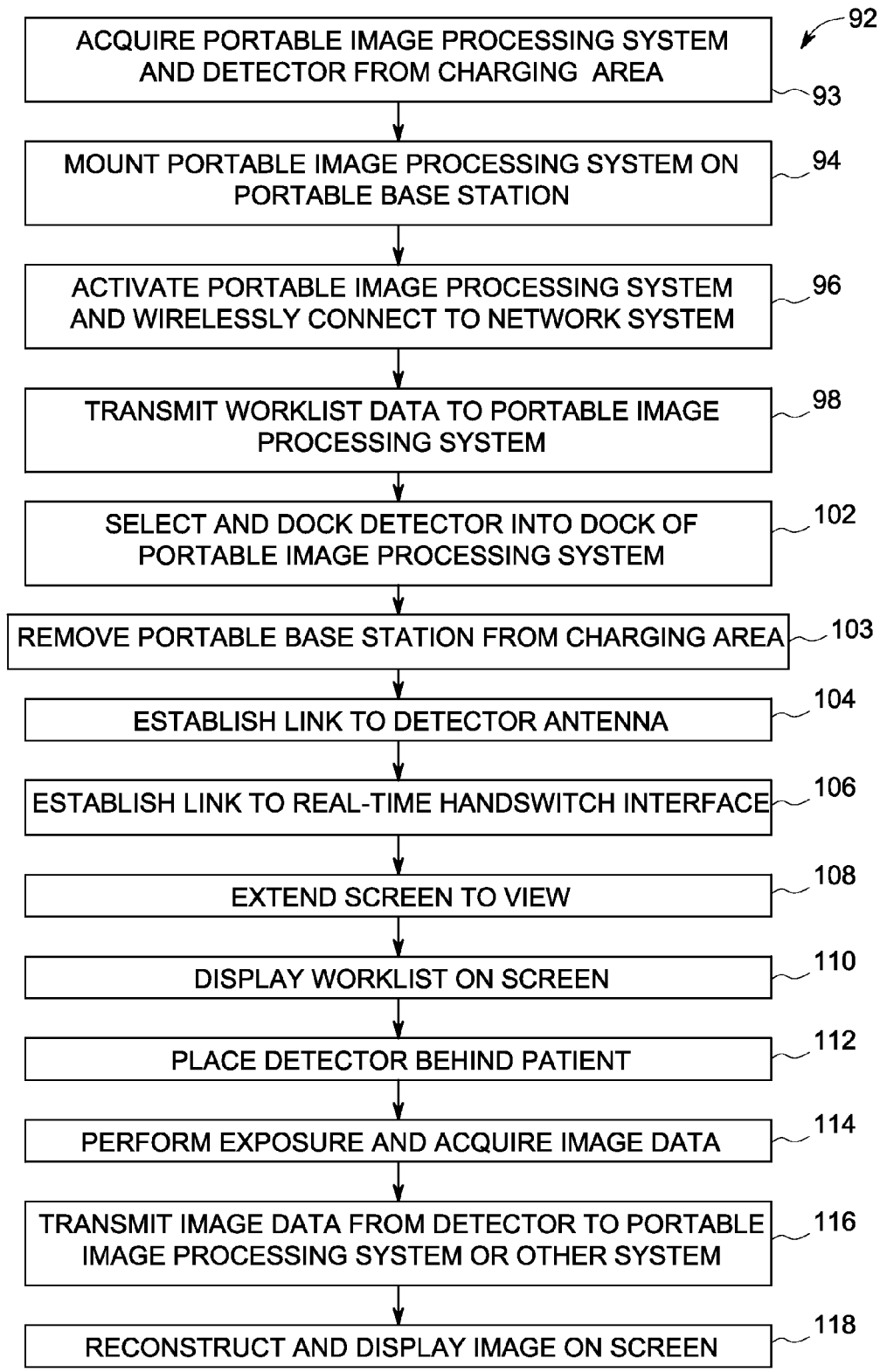
FIG. 4 is a flow diagram of a method for operating a portable radiological imaging system, in accordance with aspects of the present technique.

To illustrate the use of the portable image processing system 14, FIG. 4 is a flow diagram of an exemplary method 92 for the operation of the portable radiological imaging system 10. The method 92 includes mounting the portable processing system 14 within the holder 26 of the portable base station 12 (block 94). Prior to this the portable image processing system 14 may be acquired from a charging station located within the medical facility (block 93). Upon insertion within the holder 26, the image processing system 14 becomes active and connects wirelessly with the medical facility network system 70 via the wireless receiver 56 located on the system 14 (block 96). The network system 70 wirelessly transmits worklist data, including image sequences to be performed, to the portable image processing system 14 (block 98). The screen 62 of the portable image processing system 14 may be stowed during insertion, activation, and acquisition of the worklist. The user selects a detector 16 to use and to dock within the dock 66 of the portable image processing system 14 (block 102). The detector 16 may also be acquired from a charging station located within the facility (block 93). Upon selection of the detector 16, the portable base station 12 with the image processing system 14 and detector 16 may be removed from the charging area (block 103). After docking the detector 16, the user or system 14 establishes a link to the detector antenna (block 104). The link to the detector antenna may be wirelessly established by the system 14 directly or alternatively by user through wired connection. In addition, link is established via a wired or wireless connection between the portable image processing system 14 and the real-time handswitch interface 28 (block 106). It is noted that the wireless interface to detector 16 and handswitch interface 28 may utilize any suitable wireless communication protocol, such as an ultra wideband (UWB) communication standard, a Bluetooth communication standard, or any 802.11 communication standard or may also use IR (infrared) communication technology. With this simple preparation, the imaging technician is ready to proceed on rounds for imaging of patients on the worklist, or the system may be made available for immediate use, such as in an emergency room.

To begin image acquisition, the screen 62 is extended for viewing (block 108). Upon extension of the screen 62, the computer 58 is switched from a lower power to full power and the screen 62 is illuminated. Also, upon extension the acquired worklist is displayed on the screen 62 (block 110). Next, the detector 16 is placed in position behind the patient 40 (block 112). The user then follows the desired acquisition instructions and protocol from the worklist. Following any needed setup or positioning of the patient 40, detector 16, base station 12, and source 18, an exposure is performed and image data acquired (block 114). The image data is wirelessly transferred from the detector 16 to the portable image processing system 14 or directly to another system (block 116). For example, the image data may be processed first on image processing system 14 or directly transferred wirelessly directly to the medical facility network system 70 and to PACS 72. Upon receiving the image data, the portable image processing system 14 or other system reconstructs an image from the image data and the image is displayed on the system's screen 62 or another remote screen (block 118).

The above portable image processing system 14 allows the full use of digital radiography on existing X-ray base stations 12 with only a few modifications to those stations 12, while still allowing the stations 12 to be used for conventional radiography. In addition, the wireless detector 16 used in conjunction with the wireless communication capabilities of the portable image processing system 14 allows for the improved workflow in the hospital environment.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A portable radiological imaging system, comprising:
a portable base station having an X-ray source and a power supply;
a wireless X-ray detector configured to receive X-ray radiation from the source and to generate image data representative of an anatomical region based upon the received radiation;
a portable image processing system removably carried by the base station and configured to receive the image data from the detector and to process the image data to produce and display a user-viewable image derived from the image data, wherein the portable image processing system is separate from the detector.

2. The system of claim 1, wherein the image processing system is received in a holder within the base station.

3. The system of claim 2, wherein the image processing system is not coupled to the base station other than being physically held in the holder.

4. The system of claim 2, wherein the imaging system comprises a handswitch interface capable of sensing the reception of the image processing system into the holder and preparing for exposure control upon sensing the reception.

5. The system of claim 4, wherein the handswitch interface is capable of sensing signals related to an exposure sequence and inhibiting an exposure based on a status of the detector.

6. The system of claim 1, wherein the image processing system comprises a wireless receiver for receiving the image data wirelessly from the detector, a computer configured to execute an image reconstruction routine to derive the user-viewable image from the image data, and a user-viewable screen coupled to the computer for displaying the user-viewable image.

7. The system of claim 6, wherein the computer of the image processing system is configured to be stored in a holder of the base station during use, with the user-viewable screen extending from the holder.

8. The system of claim 7, wherein the user-viewable screen is movable between a viewing position and a stowed position, and is placed in a non-illuminated condition when in the stowed position.

9. The system of claim 6, wherein the image processing system comprises a dock for holding the detector when the detector is not in use.

10. The system of claim 9, wherein the image processing system comprises a source of electrical power, and is configured to provide power to the computer and for maintaining a charge on the detector by power from the source of electrical power.

11. The system of claim 1, wherein the image processing system is configured to receive data indicative of a hospital worklist for image sequences to be performed by displacement of the system.

12. A portable radiological imaging system, comprising:
a portable image processing system separate from and configured to be removably carried by an X-ray source base station, the processing system comprising a wireless receiver for receiving image data representative of an anatomical region wirelessly from an X-ray detector, a computer configured to execute an image reconstruction routine to derive the user-viewable image from the image data, and a user-viewable screen coupled to the computer for displaying the user-viewable image, wherein the portable image processing system is separate from the detector.

13. The system of claim 12, wherein the image processing system comprises a dock for a wireless X-ray detector when the detector is not in use.

14. The system of claim 13, wherein the image processing system comprises a rechargeable source of electrical power, and is configured to provide power to the computer and for maintaining a charge on the detector by power from the source of electrical power.

15. The system of claim 12, wherein the computer of the image processing system is configured to be stored in a holder of the base station during use, with the user-viewable screen extending from the holder.

16. The system of claim 15, wherein the user-viewable screen is movable between a viewing position and a stowed position, and is placed in a non-illuminated condition when in the stowed position.

17. The system of claim 12, wherein the image processing system is configured to receive data indicative of a hospital worklist for image sequences to be performed by displacement of the imaging system.

18. A method for operating a portable radiological imaging system, comprising:
removably mounting a portable processing system on a portable base station, the base station comprising an X-ray source, a power supply, and a holder for the portable processing system, the portable processing system comprising a wireless receiver for receiving image data representative of an anatomical region wirelessly from an X-ray detector, a computer configured to execute an image reconstruction routine to derive the user-viewable image from the image data, and a user-viewable screen coupled to the computer for displaying the user-viewable image, wherein the portable processing system is separate from the detector.

19. The method of claim 18, comprising docking a wireless X-ray detector in a dock of the portable processing system when the detector is not in use.

20. The method of claim 19, wherein the portable processing system comprises a rechargeable source of electrical power, and wherein the method comprises providing power for operation of the computer and for maintaining a charge on the detector by power from the source of electrical power.

21. The method of claim 18, comprising extending the user-viewable screen extending from the holder during use to permit viewing of the user-viewable image.

22. The method of claim 18, comprising wirelessly transmitting the image data from a wireless X-ray detector to the portable processing system after acquisition of the image data during an imaging sequence.

23. The method of claim 18, comprising wirelessly transmitting worklist data to the portable processing system and displaying a worklist on the user-viewable screen based upon the worklist data.

* * * * *